US008779006B2

(12) United States Patent
Amador et al.

(10) Patent No.: US 8,779,006 B2
(45) Date of Patent: Jul. 15, 2014

(54) COMPOSITIONS AND METHODS FOR TREATMENT AND PREVENTION OF OSTEOARTHRITIS

(75) Inventors: Ricardo Amador, Querétaro (MX); Jorge L. Rosado, Querétaro (MX); Sandra García-Padilla, Hidalgo (MX); Miguel Ángel Duarte-Vázquez, Gto. (MX)

(73) Assignee: Nucitec S.A. de C.V., Queretaro (MX)

( * ) Notice: Subject to any disclaimer, the term of this patent is extended or adjusted under 35 U.S.C. 154(b) by 0 days.

(21) Appl. No.: 13/235,149

(22) Filed: Sep. 16, 2011

(65) Prior Publication Data
US 2012/0052131 A1 Mar. 1, 2012

Related U.S. Application Data

(62) Division of application No. 12/185,603, filed on Aug. 4, 2008.

(60) Provisional application No. 60/953,724, filed on Aug. 3, 2007.

(30) Foreign Application Priority Data

Sep. 14, 2007 (MX) .................... MX/a/2007/011256

(51) Int. Cl.
*A61K 47/12* (2006.01)
*A61K 33/10* (2006.01)
*A61K 33/14* (2006.01)

(52) U.S. Cl.
USPC ........................... 514/717; 514/782; 424/682

(58) Field of Classification Search
CPC ................................................. A61K 514/715
See application file for complete search history.

(56) References Cited

U.S. PATENT DOCUMENTS

| | | | |
|---|---|---|---|
| 3,489,572 A | | 1/1970 | Kracauer |
| 4,252,797 A | * | 2/1981 | Rosenthal ....................... 514/52 |
| 4,647,453 A | | 3/1987 | Meisner |
| 5,271,946 A | | 12/1993 | Hettche |
| 5,364,845 A | * | 11/1994 | Henderson ....................... 514/54 |
| 5,843,919 A | | 12/1998 | Burger |
| 5,856,358 A | | 1/1999 | Benetti et al. |
| 6,037,331 A | | 3/2000 | Shalaby et al. |
| 6,207,672 B1 | | 3/2001 | Thorwart et al. |
| 6,428,804 B1 | * | 8/2002 | Suzuki et al. .................. 424/426 |
| 6,559,287 B1 | * | 5/2003 | Bennett et al. ................ 530/395 |
| 7,226,909 B2 | | 6/2007 | Tamatani et al. |
| 7,671,212 B2 | | 3/2010 | Taveras et al. |
| 2003/0114416 A1 | | 6/2003 | Pulaski et al. |
| 2005/0182022 A1 | | 8/2005 | Pierce |
| 2005/0249806 A1 | | 11/2005 | Proehl et al. |
| 2005/0288235 A1 | | 12/2005 | Zhao |
| 2006/0122150 A1 | * | 6/2006 | Argentieri et al. .............. 514/54 |
| 2006/0257407 A1 | | 11/2006 | Chen et al. |
| 2007/0243251 A1 | | 10/2007 | Taneja |

FOREIGN PATENT DOCUMENTS

| | | |
|---|---|---|
| MX | PA03004965 A | 9/2003 |
| MX | PA04000854 A | 5/2004 |
| MX | PA06002927 A | 6/2006 |

OTHER PUBLICATIONS

Kron, Schweizerische Medizinische Wochenschrift 1948, 4, pp. 80-83.*
Raynauld et al., Artthritis and Rheumatism 2003, 48, pp. 370-377.*
Tishler (European Journal of Internal Medicine 2004, 15, 93-96).*
Abramson, S.B., "The role of NSAIDs in the treatment of osteoarthristis," in *Osteoarthritis*, Brandt K.D., et al., eds., Oxford University Press, Oxford, Egnland, pp. 251-258 (2003).
Bovic, V., "Autologous Chondrocyte Transplantation," *Am. Acad. Orthop. Surg.*, Annual Meeting, Day 2, Mar. 16, 2000, available online at <http://journal.medscape.com/viewarticle/420393> (as accessed Jan. 16, 2009).
Diplock, A.T., et al., "Scientific Concepts of Functional Foods in Europe: Consensus Document," *Br. J Nutr.* 81:S1-S27, Cabi Publishing, England (1999).
Halstead, C.H., "Dietary supplements and functional foods: 2 sides of a coin?," *Am. J. Clin. Nutr.* 77:1001S-1007S, American Society for Clinical Nutrition, United States (2003).
Lane, N.E., "Pain Management in Osteoarthritis: The Role of COX-2 Inhibitors," *J. Rheumatol.* 24:20-24, Journal of Rheumatology Publishing Co., Canada (1997).
Pelletier, J-P., et al., "Most recent developments in strategies to reduce the progression of structural changes in osteoarthritis: today and tomorrow," *Arthritis Res. Ther.* 8:206, BioMed Central, England (Jan. 2006).
Ramsey, S.D., et al., "Use of Alternative Therapies by Older Adults With Osteoarthritis," *Arthritis Care Res.* 45:222-227, Wiley-Liss, United States (2001).
Reich, I.R., et al., "Chapter 18: Tonicity, Osmoticity, Osmolality, and Osmolarity," in *Remington: The Science and Practice of Pharmacy 20th edition*, Limmer, D., ed., Lippincott, Williams, and Wilkins, Baltimore, Maryland, United States, pp. 246-262 (2000).
Schnitzer, T.J., "Update of ACR Guidelines for Osteoarthritis: Role of the Coxibs," *J. Pain Symptom Manage* 23:S24-S30, Elsevier, United States (2002).
Vane, J.R., et al., "Cyclooxygenases 1 and 2," *Annu. Rev. Pharmacol. Toxicol.* 38:97-120, Annual Reviews, United States (1998).
Zeisel, S.H., "Regulation of "Nutraceuticals"," *Science* 285:1853-1855, American Association for the Advancement of Science, United States (1999).
International Search Report for International Application No. PCT/IB08/03398, mailed on Dec. 4, 2009, ISA/US, Alexandria, Virginia, United States.

(Continued)

*Primary Examiner* — Sue Liu
*Assistant Examiner* — Jessica Kassa
(74) *Attorney, Agent, or Firm* — Sterne, Kessler, Goldstein & Fox P.L.L.C.

(57) ABSTRACT

The present invention is in the fields of medicine, pharmaceuticals, neutraceuticals and rheumatology. The invention provides pharmaceutical compositions for the treatment and/or prevention of osteoarthritis in mammals, particularly humans, comprising sodium bicarbonate and calcium gluconate, and optionally comprising one or more additional components. The invention also provides methods of treating or preventing osteoarthritis by administering to a mammal, preferably via intraarticular injection, one or more compositions of the invention.

10 Claims, 3 Drawing Sheets

(56) References Cited

OTHER PUBLICATIONS

Bomsztyk, K. and Calalb, M.B., "Bicarbonate Absorption Stimulates Active Calcium Absorption in the Rat Proximal Tubule," *J. Clin. Invest.* 81:1455-1461, The American Society for Clinical Investigation, Inc., United States (1988).

Buclin, T., et al., "Diet Acids and Alkalis Influence Calcium Retention in Bone," *Osteoporos. Int.* 12:493-499, International Osteoporosis Foundation and National Osteoporosis Foundation, England (2001).

Dumartheray, E.W., et al., "Bicarbonate from mineral water lowers bone resorption even in calcium sufficiency," *Int. Congr. Ser.* 1297:303-309, Elsevier B.V., Netherlands (2007).

English language translation of Kron, R. "Intraarticular Alkali Therapy," *Schweizerische Medizinische Wochenschrift* 4:80-83 (1948).

Lutz, J., "Calcium balance and acid-base status of women as affected by increased protein intake and by sodium bicarbonate ingestion," *Am. J. Clin. Nutr.* 39:281-288, American Society for Clinical Nutrition, United States (1984).

Mitsui, T., et al., "Chronic corticosteroid administration causes mitochondrial dysfunction in skeletal muscle," *J. Neurol.* 249:1004-1009, Springer-Verlag, Germany (2002).

Prié, D. and Friedlander, G., "The clinical assessment of renal function," in *Oxford Textbook of Clinical Nephrology, Third Edition*, pp. 57-58, Davison, A.M., et al., eds., Oxford University Press Inc., United States (2005).

Ross, K.A., et al., "Osteoarthritis of the Knee: Treatment by Local Injection of Salicylate Compounds," *Br. Med. J.* 1:1040-1043, BMJ Publishing Group, England (1958).

Roubenoff, R., et al., "Catabolic effects of high-dose corticosteroids persist despite therapeutic benefit in rheumatoid arthritis," *Am. J. Clin. Nutr.* 52:1113-1117, American Society for Clinical Nutrition, United States (1990).

\* cited by examiner

COMPOSITIONS AND METHODS FOR TREATMENT AND PREVENTION OF OSTEOARTHRITIS

CROSS-REFERENCE TO RELATED APPLICATIONS

The present application claims the benefit of the filing date of U.S. Provisional Application No. 60/953,724, filed Aug. 3, 2007, which is incorporated herein by reference in its entirety.

BACKGROUND OF THE INVENTION

1. Field of the Invention

The present invention is in the fields of medicine, pharmaceuticals, neutraceuticals and rheumatology. In one aspect, the invention is related to the use of compositions comprising sodium bicarbonate and calcium gluconate in methods for the treatment and/or prevention of osteoarthritis, and to the use of such compositions in the manufacture of products for such treatment and/or prevention.

2. Related Art

Osteoarthritis

Osteoarthritis (OA) is the most common joint disease in mammals and is characterized by a progressive loss of articular cartilage components, mainly proteoglycans. Over time, articular cartilage in OA has been shown to lose its mechanical resistance, elasticity and smoothness, and to be consequently worn out by the movements of the joint. This leads to reactive bone remodeling, forming osteophytes, microfractures, subchondral eburnation and pseudocysts, and the exposure of the articular end of the bone.

Clinical manifestations of OA are joint pain, stiffness in the morning or after rest, pain at night, limited motion, joint deformity, occasionally synovitis, and variables degrees of inflammation. Joint pain in OA may originate not only from synovitis, but also from stretching of the joint capsule or ligaments, periosteal irritation, trabecular microfractures, intraosseous hypertension or muscle spasms.

The disruption of the proteoglycans and glycosaminoglycan aggregation is accompanied by an increase in water in the cartilaginous matrix, diminishing its rigidity. This decreased rigidity in turn increases the vulnerability of the tissue to the mechanical and chemical damage, promoting the release of Interleukin-1 (IL-1) and nitric oxide by the chondrocytes in response to the fibronectin fragments that are formed. It also increases the release of proteases with consequent collagen degradation, destabilizing the chondral matrix and further increasing water content.

The joints that are more frequently affected by osteoarthritis are, in decreasing sequence: distal interphalangeal, first carpometacarpal, proximal interphalangeal, knees, first metatarsophalangeal, and coxofemorals.

Osteoarthritis has high prevalence and is one of the main causes of pain and incapacity in elderly people. There are no specific treatments for OA, and the treatments that are available are of high cost and are only focused on controlling and diminishing the pain and inflammation associated with OA disease (i.e., obtaining symptomatic relief) and not with controlling, diminishing or eradicating the disease itself.

Mexican patent request number PA/A/2006/002927 entitled "Derivados de iminoácidos biciclicos como inhibidores de metaloproteinasas de la matriz", describes some imino acids and derivatives thereof that may be useful in the production of pharmaceuticals for the prevention and treatment of diseases whose evolution include an increase in matrix metalloprotease activity, such as joint degenerative diseases, connective tissue diseases, periodontal disease, disorders of the locomotive system, and inflammatory or carcinogenic diseases, as well as those diseases and disorders that arise after or as a result of injuries to the joints, meniscus, kneecaps or ligaments, disruptions in healing injuries, bone metabolism disruptions, ulceration, stenosis, arthropathy, myalgia, anorexia or septic shock.

In Mexican patent request number PA/A/2004/000854 entitled "El uso de derivados de heparinoide para el tratamiento y diagnóstico de desordenes que se puedan tratar con heparinoides," some heparinoid derivative compounds useful for preventing and treating metalloproteinase-related diseases and disorders are disclosed.

Mexican patent request number PA/a/2003/004965 entitled "El use de la heparina de bajo peso molecular para el tratamiento de la osteoartrosis" discloses the use of heparin derivatives containing a chelating agent covalently bound to heparinoid and a paramagnetic cation metal from metal transition series (Sc, Ti, Cr, Mn, Fe, Co, Ni, Cu, Mo, Ru) or lanthanides. These derivatives are reported to be suitable for the production of drugs for certain therapeutic and diagnostic purposes, for localization of administered dose, and for supervision of treatment success of diseases such as osteoarthrosis and thrombosis.

U.S. Pat. Nos. 6,207,672 and 5,856,358 entitled "Cyclic and heterocyclic N-substituted α-iminohydroxamic and carboxylic acids" and "Mono- and disulfo-substituted anthraquinones and their use for the treatment of bone matrix disorders," respectively, claim the use of several compounds for OA treatment.

Currently, however, there does not exist a specific treatment for OA; there are only certain treatment strategies that are frequently used to allow the mobility of the patient, or to control and diminish the primary symptoms of the disease, such as pain and inflammation.

Some options employed in order to improve mobility are:
(a) Physical medicine and rehabilitation;
(b) Weight loss when the joints that support load are affected and the patient is also overweight;
(c) Biomechanical handling such as corsets, external prosthesis, etc.

Pharmacological Treatment of Osteoarthritis Symptoms

Pharmacological treatment of the disease symptoms of OA generally includes a variety of approaches focused on controlling and diminishing the pain associated with the disease. Among such approaches are the following options:
(a) Administration of analgesics such as paracetamole and tramadole;
(b) Administration of non-steroidal anti-inflammatory drugs (NSAIDs), viscosupplementation, corticoids and/or narcotics;
(c) Orthopedic surgery; and
(d) Experimental treatments (e.g., transplant of cartilage and mesenquitomatoses cells, administration of cytokine inhibitors (IL-1, tumor necrosis factor α (TNF-α), etc.), administration of metalloprotease inhibitors, administration of nitric oxide synthetase inhibitors, administration of growth factors and administration of chondroprotectors).

Thus, there are many treatment modalities for OA including non-pharmacological (e.g., patient education, weight control, physical and occupational therapy) and pharmacologic therapy (e.g., intraarticular steroid injections, paracetamol, topical analgesics, nonsteroidal anti-inflammatory drugs and opioid analgesics). The handling of osteoarthritis is predominantly palliative, focused in the mitigation of the symptoms such as pain and inflammation. Nevertheless, since existing therapeutic approaches do not attack the mechanism of origin OA, cartilage deterioration continues despite physical and/or pharmacological attempts to treat the disease and/or its symptoms. The most used drugs for the treatment of the osteoarthritis are the NSAIDs (Abramson S B. The role of NSAIDs in the treatment of osteoarthritis. Brandt K D, Doherty M, Lohmlander L S (Eds). Oxford University Press. 2003: 251-258; Schnitzer T J. American College of Rheumatology. Update of ACR guidelines for osteoarthritis: role of the coxibs. J Pain Symptom Manage. 2002: S24-S30), which are common analgesics that reduce pain and inflammation. This type of drug includes aspirin, ibuprofen and naproxen. They act by blocking the synthesis of prostaglandins via non-selective inhibition of the cyclooxygenase enzyme activity ("COX"; Vane J R, Bakhle Y S, Botting R M. Cyclooxygenases 1 and 2. Annu Rev Pharmacol Toxicol. 1998, 38:97-120). Although the NSAIDs are the most widely prescribed drugs to reduce joint pain and stiffness, the inflammatory component of OA occasionally is minimal; therefore, the actual need for the anti-inflammatory effects of the NSAIDs, and thus the benefit of administering such drugs, in OA treatment is controversial. Moreover, inhibition of prostaglandin biosynthesis is directly related to many common and occasionally severe side effects including gastrointestinal bleeding, hypertension, congestive hearth failure, hyperkalemia, renal insufficiency and platelet aggregation inhibition (Zeisel S H. Regulation of nutraceuticals. Science. 1999, 285; Halsted C H. Dietary supplements and functional foods: 2 sides of a coin? Am Clin Nutr. 2003, 77:1001S-1007S; Diplock A T, Aggett P J, Ashwell M, Bornet F, Fern F B, Roberfroid M B. Scientific concepts of functional foods in Europe; consensus document. Br J Nutr. 1999, 81:S1-S27). In fact in April 2005, the U.S. Food and Drug Administration (FDA) requested to the manufacturers of NSAIDs that a warning label be included on NSAID products, alerting the consumer to the increased risk of cardiovascular events and intestinal bleeding that could accompany the use of the products. These disadvantages call for an evaluation of the risks and benefits of such therapies for OA, in comparison with the less toxic (or at least less risky) approaches.

Another type of drugs, the Cyclo-oxygenase 2 (COX2) selective inhibitors, have demonstrated analgesic and anti-inflammatory efficacies in patients with OA comparable to those of traditional NSAIDs, and an improved safety profile relative to NSAIDSs (Ramsey S D, Spencer A C, Topolski T D, Belza B, Patrick D L. Use of alternative therapies by older adults with osteoarthritis. Arthritis Reum. 2001, 45:222-227). Nevertheless, numerous reports of heart attacks and adverse cerebrovascular events have led the FDA to reevaluate the risks against benefits of COX-2 inhibitors. As a result of the FDA's analysis, the COX-2 drugs rofecoxib (marketed in the US under the brand name VIOXX®) and valdecoxib (marketed in the US under the brand name EXTRA®) have been withdrawn from the market in the United States, after it was reported that an increase in heart attacks was observed in patients taking these drugs (Lane N E. Pain management in osteoarthritis: the role of COX-2 inhibitors. J rheumatol, 1997, 24:20-24). The COX-2 drug Celecoxib (marketed in the US under the brand name CELEBREX®) is still available, but only with serious warning labels and recommendations of being prescribed at low doses and during a limited period of time to avoid adverse effects.

In another therapeutic approach, the inflammation and moderate to severe joint pain associated with OA can be effectively relieved by intra-articular injection of corticosteroids. However, the long-term impact and safety of such injections, especially on knee anatomical structure, is still unknown. Thus, while the corticosteroids are a useful form of treatment for OA, the disadvantage is that the palliatory effect of corticosteroid injection appears to last for only 1 to 3 weeks and that such injections could themselves also lead to long-term joint damage. Other concerns associated with the use of corticosteroid injection include synovitis, cutaneous atrophy (local), and steroid arthropathy.

The use of natural glucosamine and chondroitin sulfate (as food additives) against degeneration of articular cartilage at other locations has recently received much attention. Most emphasis was laid upon the reported beneficial effect of glucosamine and chondroitin sulfate on OA of the knee, and the general conclusion was that the results were promising but the evidence insufficient to support a conclusion that such food additives were useful in the treatment or prevention of OA (Pelletier J P, Martell-Pelletier J, Raynauld, J P. Most recent developments in strategies to reduce the progression of structural changes in osteoarthritis: today and tomorrow. Arthritis Research and Therapy. 2006, 8:206).

One OA treatment that has demonstrated an effectiveness of 70% to 90% and produces excellent results is the transplantation of cultured autologous chondrocytes. This method consists of taking chondral cellular material from the patient and seeding it in a proper culture medium for its proliferation, and then, once enough cellular volume is achieved, implanting it in the damaged tissues to cover their defects (Vladimir B. Autologous chondrocyte transplantation. American Academy of Orthopaedic Surgeons Annual Meeting. 2000, pp. 1-6). Despite its promise, however, this approach to treating OA is an expensive and time-consuming procedure.

Another OA treatment that at the present enjoys high popularity involves the intraarticular application of commercially available artificial synovial fluid, such as HYALGAN® (Sanofi-Aventis US, Bridgewater, N.J.), ORTHOVISC® (DePuy Mitek, Inc, Raynham, Mass.), ARTZAL®/SUPARTZ® (Seikagaku Corpn., Tokyo, Japan) and SYNVISC® (Genzyme Corpn., Cambridge, Mass.). This substance acts only by modifying the rheology of the synovial fluid, producing an almost immediate sensation of free movement and pronounced reduction of pain in patients afflicted with OA. However, the effect of this artificial synovial fluid administration is temporary, because the material remains within the articular chamber for only about 72 hours before it is absorbed and metabolized. In addition, the main underlying problem causing OA is not corrected by such a treatment— that is, the cartilage is not repaired from articular damage. Hence, even with such a treatment which results in temporary alleviation of OA symptoms, joint deterioration continues.

Thus, it is clear that there is a need in the art for a more specific approach to treating and/or preventing osteoarthritis, which not only improves and alleviates the symptoms associated with OA but which also affects and reverses the underlying physiological causes of the disease.

BRIEF SUMMARY OF THE INVENTION

In one aspect, the present invention is related to the use of sodium bicarbonate and calcium gluconate for the treatment and/or prevention of osteoarthritis, as well as to pharmaceutical compositions containing such components and methods of manufacturing such compositions.

In one embodiment, the invention provides a pharmaceutical composition for the treatment of osteoarthritis in a mammal, comprising sodium bicarbonate and calcium gluconate. In certain such embodiments, the sodium bicarbonate is present at a concentration of from about 5%-10% (w/v) (more particularly, about 6%-8% (w/v), about 6%-7% (w/v), about 6.5% (w/v), or about 6.75% (w/v)), and the calcium gluconate is present at a concentration of from about 0.5%-5% (w/v) (more particularly, about 0.75%-2% (w/v), about 0.75% (w/v), about 1% (w/v), or about 1.5% (w/v)). In certain preferred embodiments, the compositions of the invention comprise about 6.5% (w/v) or about 6.75% (w/v) sodium bicarbonate and about 0.75% (w/v) or about 1.5% (w/v) calcium gluconate. In one such embodiment, the compositions comprise about 6.75% (w/v) sodium bicarbonate and about 0.75% calcium gluconate. In another such embodiment, the compositions comprise about 6.75% (w/v) sodium bicarbonate and about 1.5% (w/v) calcium gluconate. The compositions of the invention can be in any suitable dosage form, but are preferably in solid form or aqueous solution form, and most preferably are in aqueous solution form.

In additional embodiments, the invention provides such compositions of the invention which further comprise one or more additional components, particularly wherein such one or more additional components are suitable for assisting in the treatment and/or prevention of osteoarthritis. Such compositions of the invention may comprise, for example, as the one or more additional components, at least one NSAID (including but not limited to aspirin, diclofenac, aceclofenac, ketorolac, ibuprofen, flurbiprofen, ketoprofen, and naproxen, and pharmaceutically acceptable derivatives, salts or esters thereof), at least one non-steroidal immunophilin-dependent immunosuppressant ("NsIDI", including but not limited to calcineurin inhibitors such as cyclosporine, tacrolimus, ascomycin, pimecrolimus, as well as other agents (peptides, peptide fragments, chemically modified peptides, or peptide mimetics) that inhibit the phosphatase activity of calcineurin; and rapamycin (sirolimus), fujimycin (tacrolimus) and everolimus, which bind to an FK506-binding protein, FKBP-12), at least one COX-1 inhibitor (including but not limited to aspirin, ibuprofen and naproxen), at least one COX-2 inhibitor (including but not limited to celecoxib, rofecoxib, valdecoxib, lumiracoxib, meloxicam, tramadol, lumiracoxib, etoricoxib and nimesulide), at least one corticosterioid (including but not limited to betamethasone, budesonide, cortisone, dexamethasone, hydrocortisone, methylprednisolone, prednisolone, prednisone and triamcinolone), at least one glycosaminoglycan (including but not limited to glucosamine or glucosamine sulfate), at least one proteoglycan (including but not limited to heparan sulfate proteoglycan or chondroitin sulfate proteoglycan), at least one hyaluronic acid, and synovial fluid (including but not limited to HYALGAN®, ORTHOVISC®, ARTZAL®/SUPARTZ® and SYNVISC®. Additional components suitable for inclusion in the compositions of the present invention will be familiar to the ordinarily skilled artisan.

In suitable embodiments, the compositions of the present invention are formulated for oral administration or parenteral administration, and preferably for parenteral administration such as in an injectable form. In particular such embodiments, the compositions are formulated for administration to an animal, such as a mammal, via intraarticular injection.

In other embodiments, the invention provides methods of treating or preventing osteoarthritis in a mammal (such as a human), comprising administering to said mammal an osteoarthritis-treating or osteoarthritis-preventing amount of a pharmaceutical composition comprising sodium bicarbonate and calcium gluconate, such as one or more of the compositions of the invention that are described herein and above. According to suitable such methods, the compositions are administered to the mammal orally or parenterally, and preferably parenterally such as via injection. In particular such methods, the compositions are administered to the mammal via intraarticular injection. In additional embodiments, such methods of the invention further comprise administering to the mammal, preferably via intraarticular injection, a hyperosmolar solution of sodium chloride (particularly wherein the concentration of sodium chloride in the hyperosmolar solution is about 1.77 g/ml), so as to diminish the water content inside the chondral matrix and restore the loss of chlorine produced by the exchange of $HCO_3^+/Cl^-$.

Other preferred embodiments of the present invention will be apparent to one of ordinary skill in light of the following drawings and description of the invention, and of the claims.

DETAILED DESCRIPTION OF THE INVENTION

Figure 1:
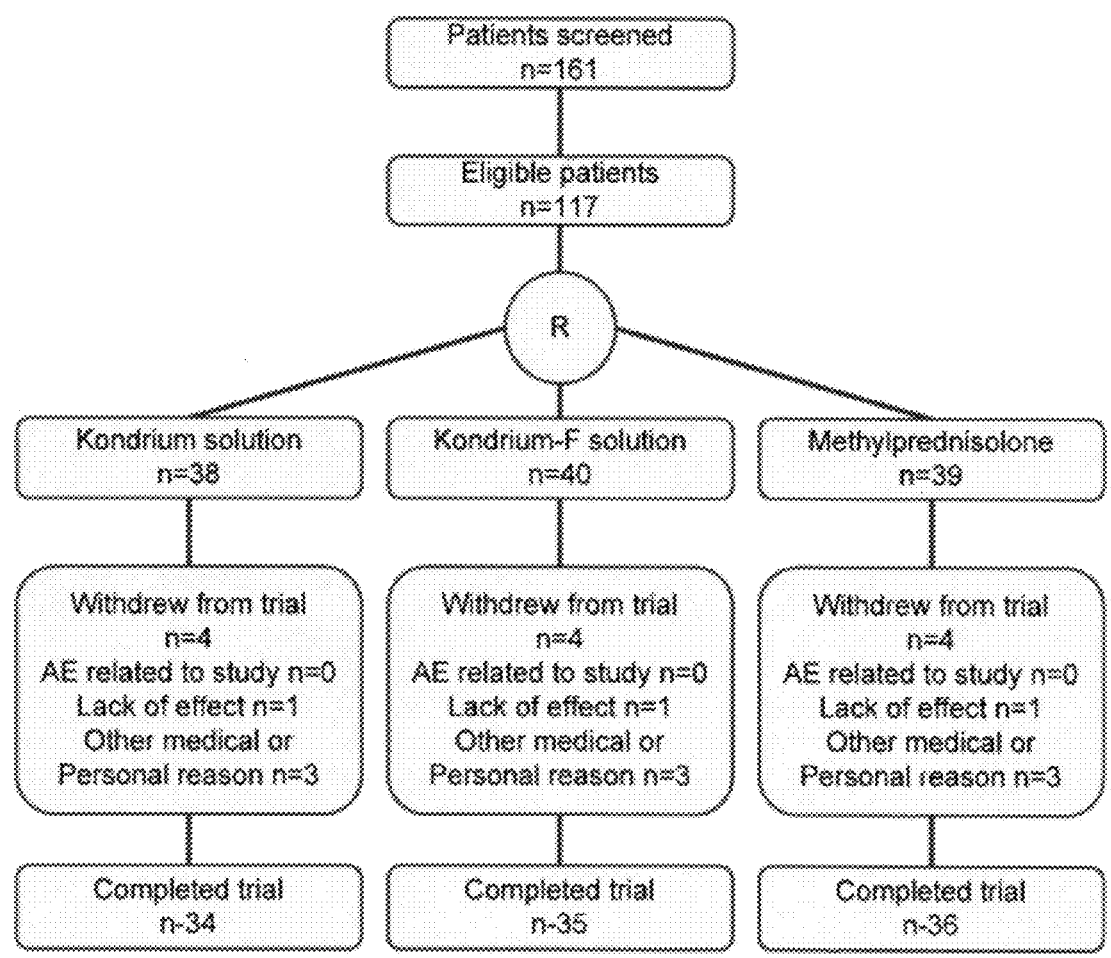
FIG. 1 is a flow chart which illustrates the method by which participants were selected for the Kondrium™/methylprednisolone study.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described hereinafter.

DEFINITIONS

About: As used herein when referring to any numerical value, the term "about" means a value of ±10% of the stated value (e.g., "about 50° C." encompasses a range of temperatures from 45° C. to 55° C., inclusive; similarly, "about 100 mM" encompasses a range of concentrations from 90 mM to 110 mM, inclusive).

Bound: As used herein, the term "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, thioester, thioether, urethane, amide, amine, peptide, imide, hydrazone, hydrazide, carbon-sulfur bonds, carbon-phosphorus bonds, and the like. The term "bound" is broader than and includes terms such as "coupled," "conjugated" and "attached."

Disease, disorder, condition: As used herein, the terms "disease" or "disorder" refer to any adverse condition of a human or animal including tumors, cancer, allergies, addiction, autoimmunity, infection, poisoning or impairment of optimal mental or bodily function. "Conditions" as used herein includes diseases and disorders but also refers to physiologic states. For example, fertility is a physiologic state but not a disease or disorder; hence, compositions suitable for preventing pregnancy by decreasing fertility would therefore be described herein as a treatment of a condition (fertility), but not a treatment of a disorder or disease. Other conditions encompassed by the use of that term herein will be understood by those of ordinary skill in the art.

Effective Amount: As used herein, the term "effective amount" refers to an amount of a given compound, conjugate or composition that is necessary or sufficient to realize a desired biologic effect. An effective amount of a given compound, conjugate or composition in accordance with the methods of the present invention would be the amount that achieves this selected result, and such an amount can be determined as a matter of routine by a person skilled in the art, using assays that are known in the art and/or that are described herein, without the need for undue experimentation. For example, an effective amount for treating or preventing osteoarthritis could be that amount necessary to prevent the development and/or progression of the symptoms and/or underlying physiological causes of osteoarthritis, such as preventing or reducing an increase in water in the cartilaginous matrix which diminishing the rigidity of the matrix, reducing or preventing joint pain or stiffness, reducing or preventing disruption of the proteoglycans and/or glycosaminoglycans in one or more joints, etc. The term is also synonymous with "sufficient amount." The effective amount for any particular application can vary depending on such factors as the disease, disorder or condition being treated, the particular composition being administered, the route of administration, the size of the subject, and/or the severity of the disease or condition. One of ordinary skill in the art can determine empirically the effective amount of a particular compound, conjugate or composition of the present invention, in accordance with the guidance provided herein, without necessitating undue experimentation.

One, a, or an: When the terms "one," "a," or "an" are used in this disclosure, they mean "at least one" or "one or more," unless otherwise indicated. As such, the terms "a" (or "an"), "one or more," and "at least one" can be used interchangeably herein.

Peptide, polypeptide, protein: As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. In accordance with this definition, polypeptides used in the present invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as "polypeptides" as used herein are fragments, derivatives, analogs, or variants of the foregoing polypeptides, and any combination thereof. Fragments of polypeptides, as that term or phrase is used herein, include proteolytic fragments, as well as deletion fragments, in addition to specific fragments discussed elsewhere herein. Variants of polypeptides useful in accordance with the present invention include fragments as described above, and also polypeptides with altered amino acid sequences due to amino acid substitutions, deletions, or insertions. Variants may occur naturally or be non-naturally occurring Non-naturally occurring variants may be produced using art-known mutagenesis techniques. Variant polypeptides may comprise conservative or non-conservative amino acid substitutions, deletions or additions. Variant polypeptides may also be referred to herein as "polypeptide analogs." Derivatives of polypeptides useful in accordance with the present invention are polypeptides which have been altered so as to exhibit additional features not found on the native polypeptide. Examples include fusion proteins, polypeptides having one or more residues chemically derivatized by reaction of a functional side group, and peptides that contain one or more naturally occurring amino acid derivatives of the twenty standard amino acids (for example, 4-hydroxyproline may be substituted for proline; 5-hydroxylysine may be substituted for lysine; 3-methylhistidine may be substituted for histidine; homoserine may be substituted for serine; ornithine may be substituted for lysine; etc.).

Treatment: As used herein, the terms "treatment," "treat," "treated" or "treating" refer to prophylaxis and/or therapy, particularly wherein the object is to prevent or slow down (lessen) an undesired physiological change or disorder, such as the development and/or progression of osteoarthritis. Beneficial or desired clinical results include, but are not limited to, alleviation of symptoms, diminishment of the extent of disease, stabilized (i.e., not worsening) state of disease, delay or slowing of disease progression, amelioration or palliation of the disease state, and remission (whether partial or total), whether detectable or undetectable. "Treatment" can also mean prolonging survival and/or increased quality of life as compared to expected survival and/or quality of life if not receiving treatment. Those in need of treatment include those already with the condition or disorder (e.g., osteoarthritis) as well as those prone to have the condition or disorder or those in which the condition or disorder is to be prevented. By "subject" or "individual" or "animal" or "patient" or "mammal," is meant any subject, particularly a mammalian subject, for whom diagnosis, prognosis, or therapy is desired. Mammalian subjects include humans and other primates, domestic animals, farm animals, and zoo, sports, or pet animals such as dogs, cats, guinea pigs, rabbits, rats, mice, horses, donkeys, mules, burros, cattle, cows, and the like.

Overview

The present invention is related to the use of sodium bicarbonate and calcium gluconate for the treatment and/or prevention of joint diseases such as osteoarthritis, as well as to pharmaceutical compositions containing such components and methods of manufacturing such compositions. In additional embodiments, the invention provides methods of use of such compositions in the manufacture of products for treatment and/or prevention of joint diseases such as osteoarthritis. According to certain such embodiments, the present invention provides for a carefully planned combination for the treatment of osteoarthritis, for example by administration of a solution that activates the buffer capacity of proteins that forms the cartilage (e.g., a solution of sodium bicarbonate) which promotes the organification of ionized calcium, together with a solution that allows the linkage between chondrals and bone proteins (e.g., a solution of calcium gluconate). In other embodiments, the compositions provided by the present invention may further comprise one or more additional components or compounds that are useful in treating or preventing joint diseases such as OA, and/or the symptoms associated with such joint diseases; such embodiments are also described in further detail hereinbelow.

The compositions and methods provided by the present invention not only alleviate and/or remedy the symptoms of joint diseases such as OA (e.g., joint pain and inflammation), but also attacks the different factors that gives rise to joint diseases such as OA and thereby alleviates, treats and/or eradicates the underlying physiological causes of the symptoms and disease state itself. The simple and low cost compositions and methods useful for treating and/or preventing joint diseases such as OA, provided by the present invention, were developed based on the restoration of the articular surface of the synovial joints after cartilage loss or degeneration. As described hereinbelow, certain such embodiments of the invention involve administration, such as via intraarticular injection, of a solution comprising sodium bicarbonate and calcium gluconate, particularly aqueous compositions wherein the sodium bicarbonate concentration ranges from 0.1% (w/v) to 99.9% (w/v) (particularly about 6.5% (w/v) or about 6.75% (w/v)), and the calcium gluconate concentration ranges from 0.1% (w/v) to 99.9% (w/v) (particularly about 0.75% (w/v) to about 1.5% (w/v)). In certain such embodiments, the sodium bicarbonate is present at a concentration of from about 5%-10% (w/v) (more particularly, about 6%-8% (w/v), about 6%-7% (w/v), about 6.5% (w/v), or about 6.75% (w/v)), and the calcium gluconate is present at a concentration of from about 0.5%-5% (w/v) (more particularly, about 0.75%-2% (w/v), about 0.75% (w/v), about 1% (w/v), or about 1.5% (w/v)). In certain preferred embodiments, the compositions of the invention comprise about 6.5% (w/v) or about 6.75% (w/v) sodium bicarbonate and about 0.75% (w/v) or about 1.5% (w/v) calcium gluconate. In one such embodiment, the compositions comprise about 6.75% (w/v) sodium bicarbonate and about 0.75% calcium gluconate. In another such embodiment, the compositions comprise about 6.75% (w/v) sodium bicarbonate and about 1.5% (w/v) calcium gluconate.

While not wishing to be bound to any particular theory, it is believed that one of the components of the compositions of the present invention, sodium bicarbonate, works in the present compositions and methods by activating the buffer capacity of certain proteins in the joint, thereby allowing the linkage of ionized calcium (calcium organification) to the chondral and bony proteins in the joint, which in turn strengthens the joint and bone matrix. In this way, it is believed that sodium bicarbonate stimulates the buffer capacity of chondral and bone proteins in order to produce the organification of ionized calcium of those proteins.

Similarly, while not wishing to be bound to any particular theory, it is believed that another of the components of the compositions of the present invention, calcium gluconate, works in the present compositions and methods to promote the linkage between chondral proteins in the joint, thereby forming a coverage over the subchondral bone which limits the further disruption of proteins within the joint and surrounding bone matrix. In this way, it is believed that calcium gluconate promotes the linkage between chondral and bony proteins, which thereby favors the formation of an interface covering the subchondral bone, limiting the disruption of proteins and increasing the structural rigidity of the bony and cartilaginous matrix.

Using the compositions and methods of the present invention as described herein, joint pain associated with joint diseases such as OA is diminished and the articular mobility is improved. The water accumulation inside the matrix and the hypochloremia in the extracellular liquid as a result of bicarbonate administration can also be regulated by the administration of a hyperosmolar solution of sodium chloride (preferably at a concentration of about 1.7 g/ml to about 2.0 g/ml, more preferably at a concentration of about 1.75 g/ml to about 1.85 g/ml, and still more preferably at a concentration of about 1.77 g/ml).

The compositions and methods provided by the present invention can be used not only for the treatment and/or prevention of OA, but also for the treatment and/or prevention of any other inflammatory disease that produces joint damage. Additionally, the use of the compositions and methods of the present invention is not restricted to human beings; they can be also used in any mammal, alone or in combination with any other medicine or pharmaceutically active compound designed for the treatment of joint disease symptoms, or any other substance that is capable of intraarticular administration. Such uses and additional compositions are also described in detail hereinbelow.

Compositions

Thus in one embodiment, the invention provides a pharmaceutical composition for the treatment of joint diseases, including but not limited to osteoarthritis, in a mammal. Exemplary pharmaceutical compositions according to this aspect of the invention comprise sodium bicarbonate and calcium gluconate. In certain such embodiments, the sodium bicarbonate is present at a concentration of from about 0.1% to about 99.9% (w/v); suitably from about 1% to about 50% (w/v) or about 2.5% to about 25% (w/v); more suitably about 5% to about 10% (w/v); and still more suitably about 6% to about 8% (w/v), about 6% to about 7% (w/v), about 6.75% (w/v), or about 6.5% (w/v)). Similarly, in certain such embodiments, the calcium gluconate is present at a concentration of from about 0.1% to about 99.9% (w/v), suitably from about 0.25% to about 50% (w/v), about 0.5% to about 25% (w/v), about 0.5% to about 10% (w/v) or about 0.5% to about 5% (w/v); more suitably, from about 0.75% to about 2% (w/v); still more suitably about 0.75% (w/v) to about 1.5% (w/v); and still more suitably about 0.75% (w/v), about 1% (w/v), or about 1.5% (w/v)). In particularly preferred embodiments, the compositions of the invention comprise about 6.75% (w/v) sodium bicarbonate and about 0.75% (w/v) calcium gluconate. In another particularly preferred embodiment, the compounds of the present invention comprise about 6.75% (w/v) sodium bicarbonate and about 1.5% (w/v) calcium gluconate.

In additional embodiments, the compositions of the invention can further comprise one or more additional components, particularly wherein such one or more additional components are suitable for assisting in the treatment and/or prevention of osteoarthritis. Such compositions of the invention may comprise, for example, as the one or more additional components, at least one NSAID (including but not limited to aspirin, ibuprofen, aceclofenac, diclofenac, naproxen, etodolac, flurbiprofen, fenoprofen, ketoprofen, suprofen, fenbufen, fluprofen, tolmetin sodium, oxaprozin, zomepirac, sulindac, indomethacin, piroxicam, mefenamic acid, nabumetone, meclofenamate sodium, diflunisal, flufenisal, piroxicam, ketorolac, sudoxicam and isoxicam, and pharmaceutically acceptable derivatives, salts or esters thereof).

In additional embodiments, the compositions of the invention may further comprise at least one non-steroidal immunophilin-dependent immunosuppressant. By a "non-steroidal immunophilin-dependent immuno-suppressant" or "NsIDI" is meant any non-steroidal agent that decreases proinflammatory cytokine production or secretion, binds an immunophilin, or causes a down regulation of the proinflammatory reaction. NsIDIs suitable for inclusion in the present compositions include, but are not limited to, calcineurin inhibitors, such as cyclosporine, tacrolimus, ascomycin, pimecrolimus, as well as other agents (peptides, peptide fragments, chemically modified peptides, or peptide mimetics) that inhibit the phosphatase activity of calcineurin. NsIDIs also include rapamycin (sirolimus) and everolimus, which bind to an FK506-binding protein, FKBP-12, and block antigen-induced proliferation of white blood cells and cytokine secretion).

In additional embodiments, the compositions of the invention may further comprise at least one COX-1 inhibitor (including but not limited to aspirin, ibuprofen and naproxen).

In additional embodiments, the compositions of the invention may further comprise at least one COX-2 inhibitor (including but not limited to celecoxib, rofecoxib, valdecoxib, lumiracoxib, meloxicam, tramadol, lumiracoxib, etoricoxib and nimesulide, and the like).

In additional embodiments, the compositions of the invention may further comprise at least one corticosterioid (including but not limited to betamethasone, budesonide, cortisone, dexamethasone, hydrocortisone, methylprednisolone, prednisolone, prednisone and triamcinolone).

In additional embodiments, the compositions of the invention may further comprise at least one glycosaminoglycan (including but not limited to glucosamine or glucosamine sulfate).

In additional embodiments, the compositions of the invention may further comprise at least one proteoglycan (including but not limited to heparan sulfate proteoglycan or chondroitin sulfate proteoglycan).

In additional embodiments, the compositions of the invention may further comprise at least one hyaluronic acid.

In additional embodiments, the compositions of the invention may further comprise synovial fluid, such as artificial synovial fluid. Synovial fluids suitable for use in accordance with the present invention are available commercially, including but not limited to HYALGAN® (Sanofi-Aventis US, Bridgewater, N.J.), ORTHOVISC® (DePuy Mitek, Inc, Raynham, Mass.), ARTZAL®/SUPARTZ® (Seikagaku Corpn., Tokyo, Japan) and SYNVISC® (Genzyme Corpn., Cambridge, Mass.).

In other embodiments, the compositions of the invention further comprise combinations of two or more of the additional components described above. Further additional components suitable for inclusion in the compositions of the present invention will be familiar to the ordinarily skilled artisan.

The concentrations, absolute amounts and relative amounts (i.e., relative to the concentration or absolute amounts of sodium bicarbonate and calcium gluconate) of the additional one or more compounds or agents that are optionally included in the compositions of the invention will be familiar to one of ordinary skill in the art. For example, the additional compounds or agents (e.g., one or more corticosteroids, one or more NSAIDs, one or more NsIDIs, one or more COX-1 or -2 inhibitors, etc.), can be present in any amount, for example about 0.01% to about 99% (e.g., about 0.01%, about 0.1%, about 1%, about 10%, about 20%, about 30%, about 40%, about 50%, about 60%, about 70%, about 80%, or about 90%), on a weight/volume (w/v) or weight/weight (w/w) basis, relative to the concentration or absolute amounts of sodium bicarbonate and calcium gluconate that are present in the compositions.

The compositions of the invention can be in any suitable dosage form, but are preferably in solid form or aqueous solution form, and most preferably are in aqueous solution form such as in a buffered salt solution comprising one or more physiologically acceptable salts, buffers and/or carriers, such as a sufficient amount of a pharmaceutically acceptable buffer to maintain the pH of the composition within a range of from about 4.5 to about 7.4, a sufficient amount of an isotonicity agent to yield an osmolality of about 220 mosmol/kg to about 350 msomol/kg and QS water. The compositions of the present invention that are provided in solution form may optionally be preserved, aseptically manufactured and/or sterilized, for example, by filtration through a bacterial-retaining filter. While preservatives are useful in limiting concerns related to chemical degradation or bacterial growth in the liquid formulations of the present invention, the presence of these preservatives can themselves cause stinging, inflammation or irritation. Therefore, in order to reduce the possibility of such adverse events, in one embodiment, the liquid dosage forms disclosed herein can be prepared free, or substantially free, of preservatives. As used herein the phrase "free, or substantially free, of preservatives" means that the liquid formulations contain less than about 0.0001% (weight/volume) of a preservative, more suitably less than about 0.00001% (weight/volume) of a preservative, and most suitably, no preservative.

The formulations to be used for in vivo administration must be sterile. This is readily accomplished by filtration through sterile filtration membranes. Use of such membrane filters can eliminate the need for preservatives in the various liquid formulations of the present invention. However, certain liquid compositions of the invention may further comprise one or more preservatives and/or one or more stabilizers. Preservatives that are suitable for use in the compositions of the invention include, but are not limited to, edetic acid and their alkali salts such as disodium EDTA (also referred to as "disodium edetate" or "the disodium salt of edetic acid") and calcium EDTA (also referred to as "calcium edetate"), benzyl alcohol, methylparaben, propylparaben, butylparaben, chlorobutanol, phenylethyl alcohol, benzalkonium chloride, thimerosal, propylene glycol, sorbic acid, and benzoic acid derivatives. The preservatives should be used at a concentration of from about 0.001% to about 0.5% (w/v) in the final composition. The combination of benzalkonium chloride, used at a concentration of from about 0.001% to about 0.5% or preferably from about 0.005% to about 0.1% (w/v), and edetic acid (as a disodium salt), used at a concentration of from about 0.005% to about 0.1% (w/v), are the preferred preservative/stabilizer combination used in the compositions of the present invention.

In other embodiments, preservative-free liquid formulations and compositions of the present invention can also be provided in single unit-dose containers. Such containers are acceptable to deliver the therapeutic dose of the compositions of the invention, particularly topically, orally, transdermally or via injection. In certain such embodiments of the invention, the compositions can be effectively contained in a package comprising a container with a volume capacity of about 1 mL to about 10 mL. In other such embodiments of the invention, particularly those in which the compositions of the invention are provided in a dosage form suitable for parenteral administration, e.g., via intraarticular injection, the compositions can be effectively contained in a package comprising a syringe containing one or more of the compositions of the invention, particularly wherein the syringe containing the composition is itself contained within sterile packaging; in such embodiments, the sterile packaging is opened, and the composition of the invention is delivered to the affected joint of the patient, e.g., via intraarticular injection, and the syringe and packaging are then discarded. This use of single unit-dose containers eliminates the concern of contamination for the user (or other outside sources), as once the unit-dose container is opened and a single dose of the present formulations or compositions is delivered, the container is discarded.

The compositions of the present invention can be administered to a patient via any suitable mode of administration, including orally, buccally, topically, transdermally, sublingually, parenterally or the like. In certain embodiments, the compositions are administered directly to the joint in which osteoarthritis or another joint disease or disorder has manifested itself. Such administration can be accomplished via topical or transdermal administration using approaches and mechanisms described elsewhere herein and others that will be familiar to the ordinarily skilled artisan. Such direct administration to the joint can also be accomplished via direct intraarticular injection of one or more compositions of the invention into the afflicted joint or the surrounding articular space. Methods of intraarticular injection of pharmaceutical compositions are well within the level of skill of the ordinarily skilled artisan, and are also described hereinbelow.

Thus, in certain embodiments, the compositions of the invention may be formulated into forms for oral administration, including solid dosage forms or liquid dosage forms. In alternative embodiments, the compositions of the invention may be formulated into forms for direct administration to the mucosa, including the buccal mucosa (i.e., buccal administration) or oral mucosa under the tongue (i.e., sublingual administration). Solid dosage forms for oral administration include capsules, tablets, pills, powders, particles and granules. In such solid dosage forms, the compositions of the invention are mixed with at least one pharmaceutically acceptable excipient or carrier such as (a) fillers or extenders such as starches, lactose, sucrose, glucose, mannitol, dicalcium phosphate and microcrystalline cellulose; (b) binders such as sodium carboxymethylcellulose, alginates, gelatin, polyvinylpyrrolidone, and acacia; (c) disintegrating agents such as agar-agar, calcium carbonate, potato or tapioca starch, alginic acid, certain silicates, sodium carboxymethyl cellulose, pregelatinized starch and sodium starch glycolate; (d) lubricants such as calcium stearate, magnesium stearate, stearic acid, solid polyethylene glycols, sodium lauryl sulfate, and mixtures thereof; and/or (e) glidants such as talc, silicon dioxide and starch. In the case of capsules, tablets and pills, the dosage form may also comprise buffering agents. Solid compositions of a similar type may also be employed as fillers in soft and hard filled gelatin capsules using such excipients as lactose or milk sugar as well as high molecular weight polyethylene glycols, oils and the like. The solid dosage forms of tablets, dragees, capsules, pills, and granules can be prepared with coatings or shells such as enteric coatings and other coatings that are well known in the pharmaceutical formulating art. The solid dosage forms also may optionally contain opacifying, coloring and/or flavoring agents, and can also be formulated such that they release the active ingredient(s) only, or preferentially, in a certain part of the intestinal tract, optionally in a delayed manner (see U.S. Pat. No. 5,271,946, the disclosure of which is incorporated herein by reference in its entirety). Examples of embedding compositions which can be used include polymeric substances and waxes. The active compounds can also be in micro-encapsulated form, if appropriate, with one or more of the above-mentioned excipients.

In other embodiments, the compositions of the invention are formulated into dosage forms suitable for parenteral administration. For example, liquid dosage forms of the compositions of the present invention that are suitable for parenteral (including via injection) or oral administration include pharmaceutically acceptable emulsions, solutions, suspensions, syrups and elixirs. In addition to the active compound(s), the liquid dosage forms may contain inert diluents and/or solvents commonly used in the art. Water is the solvent of choice for the formulations of the invention; however, combinations of water with other physiologically acceptable solvents as required are also satisfactory for use. Other solvents, solubilizing agents and emulsifiers suitable for use in place of, or in addition to, water include but are not limited to saturated aliphatic mono- and polyvalent alcohols which contain 2-6 carbon atoms (including, but not limited to, ethanol, 1,2-propylene glycol, sorbitol, and glycerine), polyglycols such as polyethylene glycols, and surfactants/emulsifiers like the fatty acid esters of sorbitan, and mixtures thereof. Oils, in particular, cottonseed, peanut, or corn oils, may also be added to the compositions. The combination of the additional solvents in the aqueous solution should preferably not exceed about 15% (w/v) of the total composition. Besides inert diluents, the oral compositions can also include adjuvants such as wetting agents, emulsifying and suspending agents (e.g., microcrystalline cellulose, sodium carboxymethyl cellulose, hypromellose, carbopol and the like), surfactants, sweetening, flavoring, and perfuming agents, including those described in further detail herein below. Liquid dosage forms that provide the active ingredient(s) in suspension may comprise, in addition to the active compound(s), one or more suspending agents such as microcrystalline cellulose, magnesium aluminum silicate, bentonite, agar-agar, hypromellose, sodium carboxymethyl cellulose, carbopol/carbomer, pectin, acacia, tragacanth or their mixtures.

Suitable formulations for parenteral administration (e.g., via injection, particularly intraarticular injection) include aqueous solutions of the active compounds in water-soluble form, for example water-soluble salts and alkaline solutions. Alkaline salts can include ammonium salts prepared, for example, with Tris, choline hydroxide, bis-Tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

Certain compositions of the invention may further comprise one or more solubility-enhancing agents that are used to improve the solubility of the compound(s) used as active ingredients in the compositions of the invention. Solubility-enhancing agents that are suitable for use in the compositions of the invention include, but are not limited to, polyvinylpyrrolidone (preferably grades 25, 30, 60, or 90), poloxamer, polysorbate 80, sorbitan monooleate 80, and polyethylene glycols (molecular weights of 200 to 600).

Certain compositions of the invention may further comprise one or more agents that are used to render the composition isotonic, particularly in those compositions in which water is used as a solvent. Such agents are particularly useful in compositions formulated for parenteral administration, particularly via intraarticular injection, since they adjust the osmotic pressure of the formulations to the same osmotic pressure as the injection site. Agents that are suitable for such a use in the compositions of the invention include, but are not limited to, sodium chloride, sorbitol, propylene glycol, dextrose, sucrose, and glycerine, and other isotonicity agents that are known in the art (see, e.g., Reich et al., "Chapter 18: Tonicity, Osmoticity, Osmolality and Osmolarity," in: Remington: The Science and Practice of Pharmacy, 20th Edition, Lippincott Williams and Wilkins, Philadelphia, Pa. (2000)).

It is desirable that the compositions of the present invention that are to be administered in liquid form (including orally, topically or parenterally applied formulations) have a pH of about 4.5 to about 7.8, and preferably have a pH of about 5.5 to about 7.4, for physiological reasons. Accordingly, in additional embodiments, the compositions of the invention may further comprise one or more buffering agents or combinations thereof, that are used to adjust and/or maintain the compositions into the desired pH range. Adjustment of pH or buffering agents that are suitable for use in the compositions of the invention include, but are not limited to, citric acid, sodium citrate, sodium phosphate (dibasic, heptahydrate form), and boric acid or equivalent conventional buffers, or combinations thereof. The appropriate amounts of buffers and buffering agents, or combinations thereof, that are to be used in the compositions of the invention are readily determined by those of ordinary skill without undue experimentation, particularly in view of the guidance contained herein and in standard formularies such as the United States Pharmacopoeia, Remington: The Science and Practice of Pharmacy, and the like, the disclosures of which are incorporated herein by reference in their entireties.

Methods of Use

In additional embodiments of the invention, the compositions of the present invention can be used therapeutically in regimens for treating mammals afflicted with certain diseases, particularly with certain joint disorders such as osteoarthritis and other such disorders described elsewhere herein and that will be familiar to the ordinarily skilled artisan. Thus, in additional embodiments, the invention provides methods of treating or preventing a joint disease or disorder such as osteoarthritis in a mammal (such as a human), comprising to administering to said mammal an osteoarthritis-treating or osteoarthritis-preventing amount of a composition comprising sodium bicarbonate and calcium gluconate, and optionally further comprising one or more additional components useful in treating or preventing a joint disease and/or the symptoms associated therewith. In related embodiments, the invention provides methods of reducing or preventing the progression of a joint inflammation or injury to a more advanced degenerative joint disease, such as OA, in a patient, comprising administering to the patient a therapeutically effective amount of one or more of the compositions of the present invention. Compositions suitable for accomplishing such methods of the invention include the compositions of the invention that are described herein.

According to certain such methods of the invention, one or more compositions of the present invention are administered to a patient, such as a patient suffering from or predisposed to osteoarthritis or a similar joint disease, via any suitable mode of administration, including orally, buccally, topically, transdermally, sublingually, parenterally or the like. In certain embodiments, the compositions are administered directly to the joint in which osteoarthritis or another joint disease or disorder has manifested itself. Such administration can be accomplished via topical or transdermal administration using approaches and mechanisms described elsewhere herein and others that will be familiar to the ordinarily skilled artisan. According to other suitable such methods, the compositions are administered to the mammal orally or parenterally, and preferably parenterally such as via injection.

In particular such methods, the compositions are administered to the mammal via intraarticular injection into the afflicted joint or the surrounding articular space. Methods of intraarticular injection of pharmaceutical compositions are well within the level of skill of the ordinarily skilled artisan, and are also described hereinbelow.

Suitable dosages (e.g., amounts, volumes, etc.) of the compositions of the invention will be apparent from the Examples below. In certain embodiments, a per injection volume of between about 2 mL to about 10 mL (suitably about 2 mL, about 2.5 mL, about 3 mL, about 3.5 mL, about 4 mL, about 4.5 mL, about 5 mL, about 5.5 mL, about 6 mL, about 6.5 mL, about 7 mL, about 7.5 mL, about 8 mL, about 8.5 mL, about 9 mL, about 9.5 mL or about 10 mL) of one or more of the compositions of the present invention is introduced into the mammal. Other suitable dosages will be readily apparent to those of ordinary skill based on the disclosure herein and knowledge that is readily available to the ordinarily skilled artisan.

In additional embodiments, such methods of the invention further comprise administering to the mammal, preferably via intraarticular injection, a hyperosmolar solution of sodium chloride, preferably wherein the solution is prepared according to the methods described above for preparation of the compositions of the invention. Thus, in conjunction with administration of one or more of the compositions of the invention to the patient, the patient is also administered a hyperosmolar solution of sodium chloride at the same site as the administration of the one or more compositions of the invention. By "in conjunction with administration of one or more compositions of the invention" is meant that the hyperosmolar sodium chloride composition is administered contemporaneously with (i.e., just prior to, at the same time as, or just after) the administration to the patient of one or more compositions of the invention, or some time later such as at the end of a multi-month regimen of administration of the compositions of the invention, to the patient. In suitable such embodiments, the concentration of sodium chloride in the hyperosmolar solution is about 1.7 g/ml to about 2 g/ml, more suitably about 1.7 g/ml to about 2.0 g/ml or about 1.75 g/ml to about 1.85 g/ml, and still more suitably about 1.77 g/ml. Suitably, a per injection volume of between about 2 mL to about 10 mL (suitably about 2 mL, about 2.5 mL, about 3 mL, about 3.5 mL, about 4 mL, about 4.5 mL, about 5 mL, about 5.5 mL, about 6 mL, about 6.5 mL, about 7 mL, about 7.5 mL, about 8 mL, about 8.5 mL, about 9 mL, about 9.5 mL or about 10 mL) of the hyperosmolar sodium chloride solution is introduced into the mammal. While not wishing to be bound to any particular theory, it is thought that the administration of a hyperosmolar solution of sodium chloride acts to diminish the water content inside the chondral matrix, thereby reversing the loss of chlorine produced by the exchange of $HCO3^+/Cl^-$.

According to the methods of the invention, the compositions of the invention (and optionally the hyperosmolar solution of sodium chloride) can be administered to the patient according to a wide variety of dosing schedules. For example, the compositions can be administered once daily for a predetermined amount of time (e.g., four to eight weeks, or more), or according to a weekly schedule (e.g., one day per week, two days per week, three days per week, four days per week, five days per week, six days per week or seven days per week) for a predetermined amount of time (e.g., four to eight weeks, or more). A specific example of a "once weekly" dosing schedule is administration of the compositions of the invention on days 1, 8, 15 and 22 of the treatment period. In alternative embodiments the compositions of the invention may be administered intermittently over a period of months. For example, the compositions of the invention may be administered weekly for three consecutive weeks biannually (i.e., repeat the weekly dosing schedule every six months), or they may be administered once a month for a period of two, three, four, five, six, seven, eight or more months. It will be appreciated that such administration regimens may be continued for extended periods (e.g., on the order of years) to maintain beneficial therapeutic effects provided by initial treatments. In yet other embodiments, such maintenance therapy may be effected following an acute dosing regimen designed to reduce the immediate symptoms of the degenerative joint condition, disease or disorder, such as osteoarthritis. In most embodiments, however, the compositions of the invention are administered to the patient according to the methods described herein at least until the symptoms of the joint disorder or disease, such as OA, are alleviated or reduced. More commonly, the compositions of the invention and methods of the invention are used for a period of time after the symptoms are reduced to a tolerable level or completely eliminated so as to result in an improvement in the physiological structure of the joint by reducing or eliminating the underlying physiological causes of the joint disease or disorder.

The amount of the compositions of the invention administered each time throughout the treatment period can be the same; alternatively, the amount administered each time during the treatment period can vary (e.g., the amount administered at a given time can be more or less than the amount administered previously). For example, doses given during maintenance therapy may be lower than those administered during the acute phase of treatment. Appropriate dosing schedules depending on the specific circumstances will be apparent to persons of ordinary skill in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Effects of Intraarticular Administration of Anti-OA Formulation on Patient WOMAC and Lequesne Indices In the present experiments, 18 white patients, mean age of 57.8 years and diagnoses of gonartrosis grade I to V according to the Kellgren and Lawrence criteria were included in a clinical trial. The patients received intra-articular injection of 10 mL of a solution of sodium bicarbonate and calcium gluconate every month for up to 6 months. At the end of treatment an intra-articular injection of 10 mL of a 1.77 g/ml (hyperosmolar) solution of sodium chloride was administered. The clinical efficacy measure of primary interest was the pain subscale from the Western Ontario University (WOMAC) and Lequesne indexes. At the 6-months follow-up evaluations of the developed formula injected to the knees exhibited a greater symptoms improvement in 90% of the total included patients (Table 1).

TABLE 1

Changes from baseline in Womac and Lequesne Indices of patients injected with the developed formula.

| Total patients | Grade I | Grade II-III | | Grade III-IV | Grade V |
|---|---|---|---|---|---|
| N | 18 | 2 | 6 | 4 | 6 |
| | | LEQUESNE INDEX | | | |
| Baseline score | 19.72 ± 8.97 | 7.00 ± 0.00 | 20.00 ± 11.71 | 19.00 ± 1.83 | 24.17 ± 6.74 |
| Final score | 2.44 ± 4.45 | 0.00 ± 0.00 | 1.00 ± 1.26 | 3.50 ± 7.00 | 4.00 ± 5.25 |
| Change | −17.28 ± 8.27 | −7.00 ± 0.00 | −19.00 ± 10.90 | −15.50 ± 5.80 | −20.17 ± 5.91 |
| Sig | $p < 0.001$ | $p < 0.001$ | $p < 0.010$ | $p = 0.108$ | $p < 0.010$ |
| | | WOMAC INDEX | | | |
| Baseline score | 16.94 ± 10.73 | 1.40 ± 1.98 | 20.51 ± 9.87 | 13.93 ± 12.72 | 20.57 ± 7.83 |
| Final score | 0.52 ± 1.28 | 0.00 ± 0.00 | 0.62 ± 1.51 | 0.43 ± 0.85 | 0.67 ± 1.63 |
| Change | −16.42 ± 10.01 | −1.40 ± 1.98 | −19.89 ± 8.68 | −13.50 ± 11.89 | −19.90 ± 7.30 |
| Sig | $p < 0.001$ | $p < 0.001$ | $p < 0.010$ | $p < 0.050$ | $p < 0.001$ |

Example 2

Evaluation of the Comparative Efficacy of Kondrium™ and Methylprednisolone in the Treatment of Osteoarthritis of the Knee Kondrium™ is the name of an exemplary pharmaceutical composition disclosed herein and in U.S. Patent Appl. No. 60/953,724 entitled "Composition and method for the treatment and prevention of Osteoarthritis". This composition activates the buffer capacity of proteins that forms the cartilage which promotes the organification of ionized calcium, and also allows the linkage between chondrals and bone proteins. This study was designed to evaluate and compare the efficacy of Kondrium™ and methylprednisolone as active control in the treatment of osteoarthritis (OA) of knee. Methylprednisolone was chosen for comparison because at present it is the only drug medically accepted for treatment of osteoarthritis.

Methods
Study Design

This was a 16-week, randomized, double-blind, active-controlled, parallel-group study. The study received Ethics Committee approval, was performed in accordance with the ICH Harmonized Guidelines for Good clinical Practice (GPC) and the Declaration of Helsinki. All patients provided written, informed consent before the start of the study.

Patients, investigator staff, persons performing the assessment, and data analysts remained blinded to the identity of the treatment from the time of randomization until data base lock. Treatments were all identical in packaging, labeling, schedule of administration and appearance.

Patients 117 patients with OA of the knee (according to the American College of Rheumatology criteria) were included in the study. Patients were enrolled by public advertising and were studied at the San Jose Hospital in Queretaro, México. Entry criteria included: willingness to participate in the study, male and female patients aged at least 40 years of age with symptomatic evidence of OA in the knee for at least 1 year, radiographic evidence of Kellgren and Lawrence grade II to IV OA of the knee, and no intra-articular injection of corticosteroids within the last 3 months. Patients were excluded if they had: any history of adverse reaction to the study drugs, current pregnancy status, uncontrolled hypertension, active infection, undergone surgery/arthroscopy within three months, diagnosis of radiographic OA of Kellgren and Lawrence grade I.

Sample size was calculated based on the assumption of a) a minimum clinically significant change in the global score of Lequesne and WOMAC scales equal to 3.1 between the treatments and the control groups, b) a population standard deviation of the difference between Kondrium™ and methylprednisolone equal to 5.0% of the maximum pain score, c) a two-sided alpha level of 0.05, d) a beta level of 0.2 (80% power) d) and a drop-out rate of 20%. With these figures, 114 subjects were necessary according with the study design.

Concomitant treatment with analgesic (other than rescue medication) and systemic corticosteroids was not allowed during the study. Patients were permitted to use rescue medication (acetaminophen 3 g/day, paracetamol) during the study, although the use of rescue medication was prohibited before the baseline clinic visit.

Study Procedure

Participants were assessed in-person during 6 visits conducted at monthly intervals. After giving written informed consent (visit #1), patients were screened and selected according to the predetermined criteria. Visit #2 was the baseline assessment. During this visit selected patients were assigned a unique patient identification number and randomized to receive 1 intra-articular monthly injection (10 mL) of Kondrium™, Kondrium™-F or methylprednisolone (80 mg) 1 month apart during the next 3 months (visits 3, 4 and 5). Visit #3, #4 and #5 served as a midpoint assessment and visit #6 was the final assessment corresponding to the end of the intervention period of the study. Kondrium™ is an aqueous formulation that contains 6.75% (w/v) sodium bicarbonate and 0.75% (w/v) calcium gluconate. Kondrium™-F is an aqueous formulation that contains 6.75% (w/v) sodium bicarbonate and 1.5% (w/v) calcium gluconate.

Compliance with treatment was assessed by counting the number of unused vials and the number of times injection treatment was received.

Efficacy Assessments

The study's primary objective was to demonstrate the superiority of Kondrium™ and Kondrium™-F compared with methylprednisolone in the treatment of patients suffering OA in the knee. The primary efficacy variable was the change from the baseline to final assessment in the Western Ontario and McMastern University OA index (WOMAC subscale score for pain), and Lequesne's functional index.

Safety and Tolerability Assessment

Subjects were informed of all possible side effects, benefits and potential risks of the study during the first visit. Adverse reactions were monitored with health diaries, nursing assessment and clinical interviews in-person at visits #2, 3, 4, 5 and 6. Subjects were also asked to record any adverse symptoms and inform the correspondent physician immediately. All the adverse effects reported by the patient or discovered by the investigator during the study period were recorded and evaluated in terms of seriousness, severity and potential relationship to study medication. Safety assessment consisted of routine laboratory tests (haematology, biochemistry and urinalysis), measurement of vital signs and electrocardiogram recordings, which were completed at screening/baseline and at study end.

Statistical Analysis

Data analysis was performed using SPSS for Windows version 10.0. Baseline demographic variables and compliance were analyzed by means of the $\chi^2$ test. A univariate analysis of variance (ANOVA) was used to determine whether the three treatment groups differed in mean values of change from a baseline in WOMAC and Lequesne's functional index. Treatment effect is shown as the main effect controlled by the baseline values. Pairwise comparisons between treatments were done with the LSD test. All statistical tests were performed at the 0.05 level of significance.

Results

A total of 161 patients were initially screened for the study between December 2007 and February 2008. Forty-four did not meet the inclusion criteria and were excluded from the study. The remaining 117 subjects were randomly assigned to treatment with one of the three study medications (FIG. 1), and all of them received the allocated intervention. Twelve patients (10.2%) withdrew the study, 4 from the Kondrium™ group (3 due to personal reasons and 1 for unsatisfactory therapeutic effect), 4 from Kondrium™-F group (3 due to personal reason and 1 for unsatisfactory therapeutic effect) and 4 from the methylprednisolone group (3 for personal reasons and one for unsatisfactory therapeutic effect).

Figure 2:
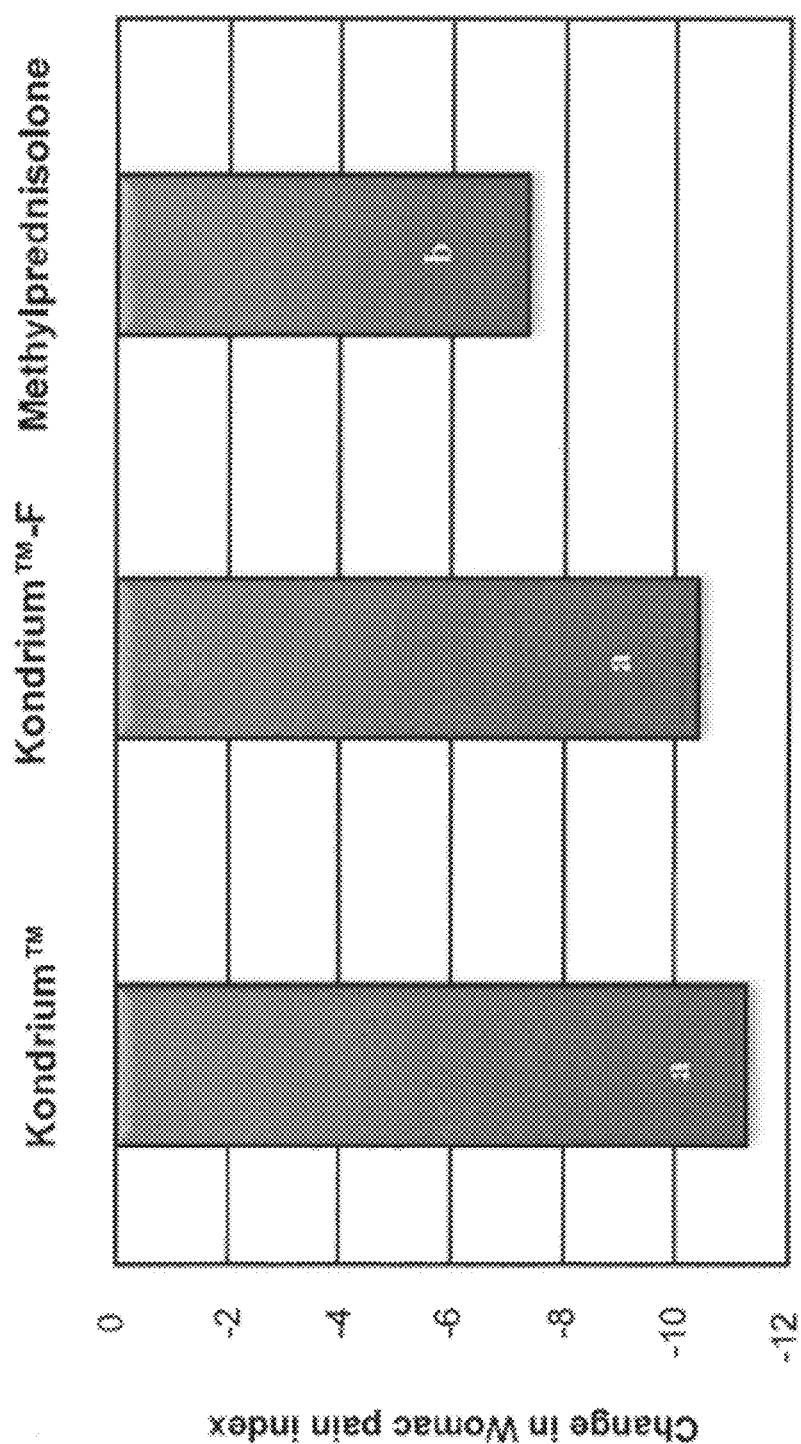
FIG. 2 is a bar graph which illustrates the change in WOMAC pain index in each treatment group evaluated after four injections. Bars with different letters are significantly different ($p<0.05$, LSD test).
Figure 3:
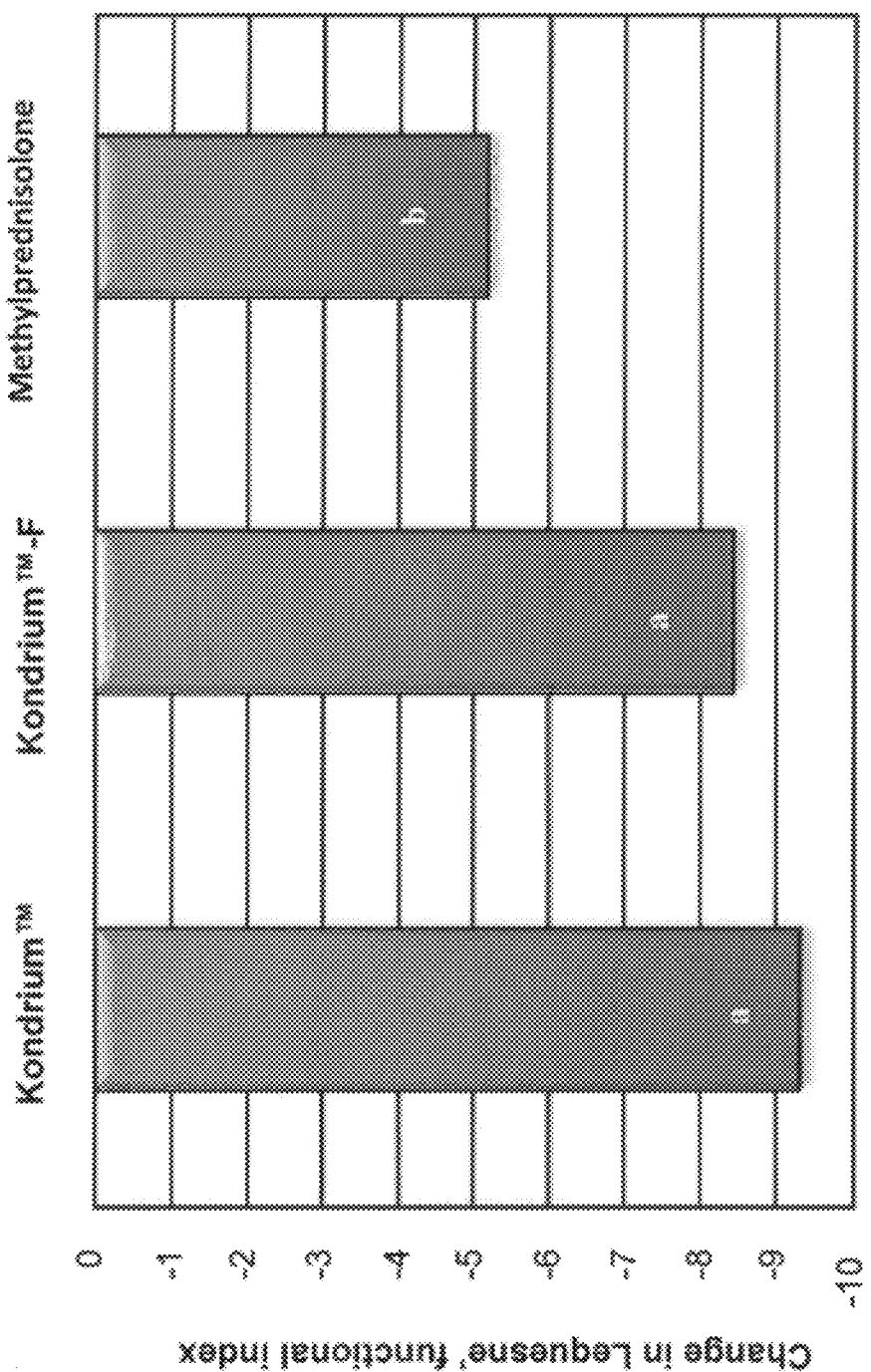
FIG. 3 is a bar graph which illustrates the change in Luquesne's functional index in each treatment group evaluated after four injections. Bars with different letters are significantly different ($p<0.05$, LSD test).

The baseline demographic characteristics of the 117 patients enrolled in the study did not differ between groups, thus were not considered to have influenced the outcome of the study (Table 2). The majority of the patients were female (80.2%), mean age was 54.7±9.06 years and mean disease duration was about 7 years. A high proportion of subjects in this study were obese, as indicated by an average body mass index greater than 30. Radiographic analysis showed no significant difference among treatment groups in the distribution of severity of joint-space narrowing and marginal osteophyte formation within each knee compartment. In the majority of the patients (80%), pain intensity in the target knee was from moderate to severe. At the end of the study, patients in all three groups showed an improvement in score for the three summary measurements of pain, stiffness and physical functioning, and for the overall WOMAC and Lequesne score with respect to the baseline (Tables 3,4). The improvement in WOMAC total score was greatest and significantly different in both the Kondrium™ and Kondrium™-F groups with respect to methylprednisolone group. The mean change in WOMAC total score was −11.28, −10.40 and −7.34 for the groups receiving Kondrium™, Kondrium™-F and methylprednisolone respectively. No differences were observed between Kondrium™ and Kondrium™-F groups (Table 3; FIG. 2). The mean changes in the Lequesne's functional index also differed significantly between the Kondrium™ and Kondrium™-F groups and the methylprednisolone group. The mean change in the Lequesne's functional index was −9.33 for the group receiving Kondrium™, −8.46 for Kondrium™-F and −5.2 for the group receiving methylprednisolone (Table 4; FIG. 3).

The percentage of patients who experienced adverse events during this study did not differ among the three groups, whereas gonalgia was the most common adverse event reported in three groups. However, gonalgia disappeared within 1-5 days.

This study was intended to evaluate the efficacy and safety of the use of intraarticular injections of Kondrium™ for the treatment of osteoarthritis of the knee. We have shown that four months of treatment with Kondrium™ or Kondrium™-F is significantly more effective than methylprednisolone with respect to changes in WOMAC total score and Lequesne's functional index. This superiority of Kondrium™ and Kondrium™-F indicates the genuine efficacy of these exemplary compositions of the present invention, which were more effective than methylprednisolone in this study.

This study also demonstrated that Kondrium™ and Kondrium™-F treatment was safe and free from serious adverse effect. The positive effect and the absence of serious adverse events of the sodium bicarbonate/calcium gluconate administration make this procedure an attractive alternative treatment for patients with oateoarthritis of the knee.

TABLE 2

Baseline demographic characteristics of patients with osteoarthritis of the knee, by study group

| | Patient group | | |
|---|---|---|---|
| | Kondrium ™ n = 34 | Kondrium ™-F n = 36 | Methylprednisolone n = 35 |
| Female (%) | 91.7 | 79.5 | 69.4 |
| Male (%) | 8.3 | 20.5 | 30.6 |
| Age, mean (SD), yr | 55.49 (9.76) | 54.46 (8.83) | 54.47 (8.81) |
| BMI, mean (SD), Kg/m² | 31.06 (4.92) | 31.63 (4.77) | 30.46 (4.86) |
| BMI > 30 (%) | 47.2 | 64.1 | 50 |

TABLE 3

WOMAC subscale measures after 4 months of treatment. *Indicate significantly different with respect to methylprednisolone group (p < 0.05, LSD test).

| | Patient group | | |
|---|---|---|---|
| | Kondrium ™ n = 34 | Kondrium ™-F n = 36 | Methylprednisolone n = 35 |
| Pain | | | |
| Baseline, mean (95% CI) | 6.15 (5.30 to 7.0) | 6.08 (5.25 to 6.91) | 4.72 (3.52 to 6.92) |
| Final, mean (95% CI) | 2.00 (1.39 to 2.61) | 2.20 (1.32 to 3.08) | 2.57 (1.70 to 3.44) |
| Change, mean (95% CI) | −3.82 (−4.61 to −3.03) | −3.59 (−4.33 to −2.86) | −2.76 (−3.52 to −2.00) |
| Stiffness | | | |
| Baseline, mean (95% CI) | 5.97 (5.24 to 6.69) | 5.98 (5.15 to 6.82) | 4.79 (3.94 to 5.64) |
| Final, mean (95% CI) | 2.11 (1.51 to 2.72) | 2.17 (1.46 to 2.89) | 2.77 (1.84 to 3.70) |
| Change, mean (95% CI | −3.65 (−4.36 to −2.94)* | −3.60 (−4.26 to −2.94)* | −2.42 (−3.10 to −1.74) |
| Physical functioning | | | |
| Baseline, mean (95% CI) | 17.80 (15.89 to 19.71) | 17.85 (15.76 to 19.93) | 14.47 (11.85 to 17.09) |
| Final, mean (95% CI) | 5.97 (4.23 to 7.72) | 6.89 (4.62 to 9.15) | 8.19 (5.48 to 10.91) |
| Change, mean (95% CI) | −11.28 (13.43 to −9.13)* | −10.40 (12.40 to −8.39)* | −7.34 (−9.41 to −5.27) |

*Significantly different from Methylprednisolone control group in a univariate analysis of variance controlled by the baseline value and LSD test for pairwise comparisons

TABLE 4

Lequesne functional index subscales measures after 4 months of treatment.
*Indicate significantly different with respect to methyl prednisolone group (p < 0.05, LSD test).

| | Patient group | | |
|---|---|---|---|
| | Kondrium ™ n = 34 | Kondrium ™-F n = 36 | Methylprednisolone n = 35 |
| Pain | | | |
| Baseline, mean (95% CI) | 5.58 (5.06 to 6.10) | 5.40 (4.93 to 5.87) | 4.34 (3.67 to 5.01) |
| Final, mean (95% CI) | 2.62 (2.04 to 3.19) | 2.40 (1.68 to 3.12) | 2.86 (2.08 to 3.64) |
| Change, mean (95% CI) | −2.65 (−3.39 to −1.92) | −2.80 (−3.48 to −2.13) | −1.96 (−2.68 to −1.25) |
| Maximum Walking Distance | | | |
| Baseline, mean (95% CI) | 4.62 (3.74 to 5.50) | 4.03 (3.38 to 4.68) | 3.24 (2.42 to 4.06) |
| Final, mean (95% CI) | 1.73 (0.95 to 2.51) | 2.07 (1.33 to 2.80) | 2.90 (2.07 to 3.72) |
| Change, mean (95% CI | −2.49 (−3.26 to −1.72)* | −1.91 (−2.62 to −1.21)* | −0.75 (−1.48 to −0.02) |
| Normal activities | | | |
| Baseline, mean (95% CI) | 8.58 (7.16 to 10.00) | 7.53 (6.70 to 8.36) | 6.93 (5.85 to 8.01) |
| Final, mean (95% CI) | 4.08 (3.37 to 4.78) | 3.90 (3.18 to 4.62) | 4.62 (3.52 to 5.72) |
| Change, mean (95% CI) | −3.87 (−4.73 to −3.01) | −3.71 (−4.50 to −2.92) | −2.80 (−3.61 to −1.99) |

*Significantly different from Methylprednisolone control group in a univariate analysis of variance controlled by the baseline value and LSD test for pairwise comparisons

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of treating osteoarthritis in a subject, comprising administering by intraarticular injection to a subject in need thereof a composition comprising sodium bicarbonate and calcium gluconate to treat the symptoms or underlying physiological causes of osteoarthritis, wherein said sodium bicarbonate is present at a concentration of from about 6%-8% (w/v).

2. The method of claim 1, wherein said sodium bicarbonate is present at a concentration of from about 6%-7% (w/v).

3. The method of claim 1, wherein said sodium bicarbonate is present at a concentration of about 6.75% (w/v).

4. The method of claim 1, wherein said sodium bicarbonate is present at a concentration of about 6.75% (w/v) and wherein said calcium gluconate is present at a concentration of about 0.75% (w/v) or about 1.5% (w/v).

5. The method of claim 1, further comprising administering by intraarticular injection to said subject of a hyperosmolar solution of sodium chloride.

6. The method of claim 5, wherein the concentration of said sodium chloride in said hyperosmolar solution is about 1.77 g/ml.

7. The method of claim 1, wherein said sodium bicarbonate is present at a concentration of about 6.75% (w/v), and wherein said calcium gluconate is present at a concentration of about 1.5% (w/v).

8. The method of claim 1, wherein said sodium bicarbonate is present at a concentration of about 6.75% (w/v), and wherein said calcium gluconate is present at a concentration of about 0.75% (w/v).

9. A method of treating osteoarthritis in a subject, comprising administering by intraarticular injection to a subject in need thereof a mixture consisting essentially of about 6.75% (w/v) sodium bicarbonate and about 1.5% (w/v) calcium gluconate to treat the symptoms or underlying physiological causes of osteoarthritis.

10. A method of treating osteoarthritis in a subject, comprising administering by intraarticular injection to a subject in need thereof a mixture consisting essentially of about 6.75% (w/v) sodium bicarbonate and about 0.75% (w/v) calcium gluconate to treat the symptoms or underlying physiological causes of osteoarthritis.

* * * * *